(12) United States Patent
Cherkassky et al.

(10) Patent No.: US 7,826,642 B2
(45) Date of Patent: Nov. 2, 2010

(54) ELECTRO-OPTICAL METHOD AND APPARATUS FOR EVALUATING PROTRUSIONS OF FIBERS FROM A FABRIC SURFACE

(75) Inventors: Arkady Cherkassky, Rishon-Lezion (IL); Amotz Weinberg, Tel Aviv (IL)

(73) Assignee: Shenkar College of Engineering and Design, Ramat Gan (IL)

( * ) Notice: Subject to any disclaimer, the term of this patent is extended or adjusted under 35 U.S.C. 154(b) by 873 days.

(21) Appl. No.: 11/783,802

(22) Filed: Apr. 12, 2007

(65) Prior Publication Data

US 2007/0248246 A1    Oct. 25, 2007

Related U.S. Application Data

(63) Continuation-in-part of application No. 10/601,858, filed on Jun. 24, 2003, now abandoned.

(60) Provisional application No. 60/390,465, filed on Jun. 24, 2002.

(51) Int. Cl.
*G06K 9/00* (2006.01)
*H04N 7/08* (2006.01)

(52) U.S. Cl. ............... 382/111; 382/321; 348/88

(58) Field of Classification Search ......... 382/100, 382/108, 111.154, 156, 162, 168, 178, 181, 382/256, 274, 276, 285, 297, 305, 321; 348/91, 348/88; 156/73.1; 700/143; 250/559, 45
See application file for complete search history.

(56) References Cited

U.S. PATENT DOCUMENTS

| | | | | |
|---|---|---|---|---|
| 5,774,177 A | * | 6/1998 | Lane | 348/88 |
| 5,936,665 A | * | 8/1999 | Vachtsevanos et al. | 348/91 |
| 6,501,086 B1 | * | 12/2002 | Leuenberger | 250/559.45 |
| 6,517,651 B2 | * | 2/2003 | Azulay | 156/73.1 |
| 6,728,593 B2 | * | 4/2004 | Hu et al. | 700/143 |
| 6,987,867 B1 | * | 1/2006 | Meier et al. | 382/111 |

* cited by examiner

*Primary Examiner*—Seyed Azarian
(74) *Attorney, Agent, or Firm*—Pearl Cohen Zedek Latzer, LLP

(57) ABSTRACT

An electro-optical method and apparatus for evaluating the dimensions of any protrusion from the threshold of the fabric surface is achieved by bending any length of fabric over a rotating roller so that the contoured area of the protrusion body above the surface can be visualized. The image of the silhouette as seen by a digital camera is processed by image processing algorithms then processed statistically and then by a neural network to yield an integrated picture of the fabric protrusions. The grading results of pilling are well correlated to the human visual method of pilling evaluation.

17 Claims, 14 Drawing Sheets

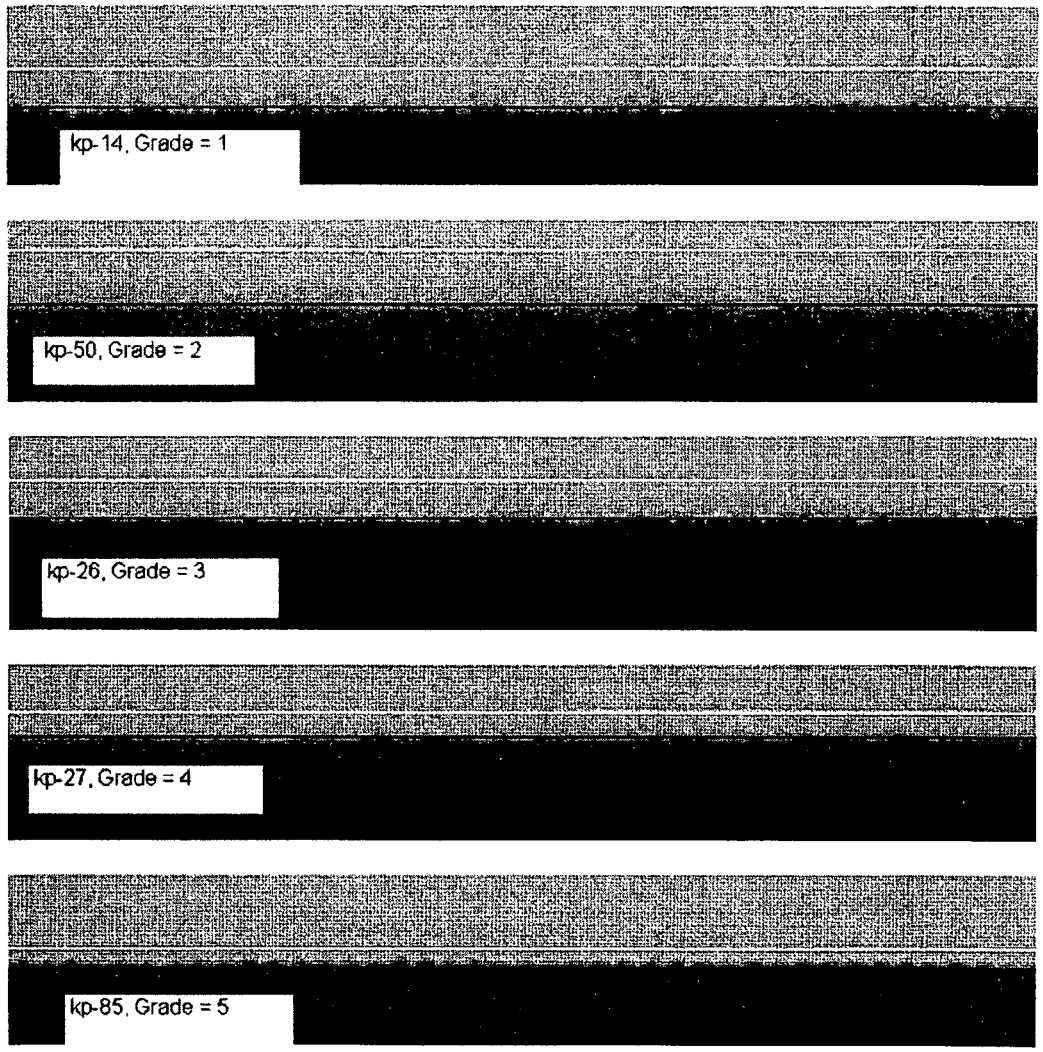
Fig. 12 Typical fabric images showing upper and lower limits of hairiness

ELECTRO-OPTICAL METHOD AND APPARATUS FOR EVALUATING PROTRUSIONS OF FIBERS FROM A FABRIC SURFACE

RELATED APPLICATIONS

This application is a Continuation-in-Part (CIP) of U.S. application Ser. No. 10/601,858 filed on Jun. 24, 2003, which in turn claims the benefit of provisional application Ser. No. 60/390,465, now abandoned filed on Jun. 24, 2002, which is incorporated in its entirety by reference herein.

BACKGROUND OF THE INVENTION

Fabric pilling is a serious problem for the textile and the apparel industry. Pilling is a fabric surface fault in which "pills" of entangled fibers protrude from the fabric surface. They give a bad appearance and can sometimes deteriorate the properties of the fabric. The development of surface hairiness may be an important factor in degrading the quality of certain fabrics and papers.

Due to the importance of the subject, the process of pill formation in fabrics by rubbing action has been thoroughly investigated. Consequently, there are many different test methods that have been developed to determine the resistance of fabrics to pilling. The measurement of pills is performed in two stages. The first entails the formation of pills by means of a laboratory test apparatus—all pill-formation apparatus is based on either tumbling or abrading the test specimen. The second stage is the evaluation of the pilling degree by subjective methods. This is done by comparing the pilled samples with a set of standard photographs or holograms that portray samples of fabrics with various degrees of pilling severity. Other methods involve the manual counting and weighing of the pills.

The pilling standards that are used to grade the samples of tested fabric are on the following scale: 5=no pills; 4=slight pilling; 3=moderate pilling; 2=severe pilling; 1=very severe pilling The development of an objective method of pill, fuzziness, snag and overall general grading is a valuable contribution to the field of fabric testing.

Methods and apparatus for inspecting fabric surfaces are quite common. Lane in U.S. Pat. No. 5,774,177 describes an apparatus for automatically detecting defects within the field of view of a video camera. The image received is then processed by a blob analysis to identify the defects. Vachtsevanos et al, in U.S. Pat. No. 5,936,665 describes an automated apparatus for counting "pills" in textile fabrics. This patent utilizes a CCD camera to capture an area of the fabric surface. The image of the surface is then processed for counting the "pills" and the data is fuzzified to determine the membership of the data in one or more of a plurality of fabric classes. In these examples and other, an area of the tested fabric is illuminated, captured by electro-optical apparatus and the data is processed to yield the characteristic data of the fabric surface.

SUMMARY OF THE INVENTION

One purpose of the present invention is to establish system, apparatus and method for automatic and objective grading of fabrics so that the resulting grading will imitate grading done by a human being. Fabric grading performed by a human examiner results several specific grading scores (for features such as pilling, fuzziness, general (pilling and fuzziness jointly) and snagging grading scores. The scores are in the span of 1-5 where 1 indicates a low score, that is the lowest (or inferior) quality and 5 a high score, which is the highest quality. The present invention relates to imperfections protruding from the fabric surface such as fibers, fuzzy, pills and yarns. The method involved is bending the fabric so that the examined surface would be examined from a side view, viewing the silhouette of the fabric at the bent line, at defined increments as it progresses along the fabric. The analysis of the image becomes one dimensional, that is the silhouette being taken depends on the width coordinate only and does not depends on the longitudinal coordinate of the specimen, and the problem of detecting all the objects on the surface of the fabric is resolved by image processing methods performed on a series of consecutive silhouette images. The grading of the pilling, fuzziness, hairiness, snags and overall general severity may be carried out using a Neural Network and/or Fuzzy Logic based classification.

The present invention describes a method, a system and an apparatus for grading the severity of the above-listed effects, such as pilling or hairiness of fabric samples that were exposed to surface friction, such as rubbing. The fabric sample is folded along its width by means of a rotating tube. A digital sensor, such as a CCD array, captures the profile of the fold and transmits the profile images to a computing unit. The fabric is further moved around the rotating tube in small defined increment and another picture is taken. This process continues until the complete sample area is scanned. The data is processed by image processing methods and the results are transformed into the existing grading scale so that the computed grading is expressed using the scale traditionally used by an expert examiner.

BRIEF DESCRIPTION OF THE DRAWING

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

FIG. 12 illustrates the typical fabric images showing upper and lower limits of hairiness, according to embodiments of the present invention.

Figure 1:
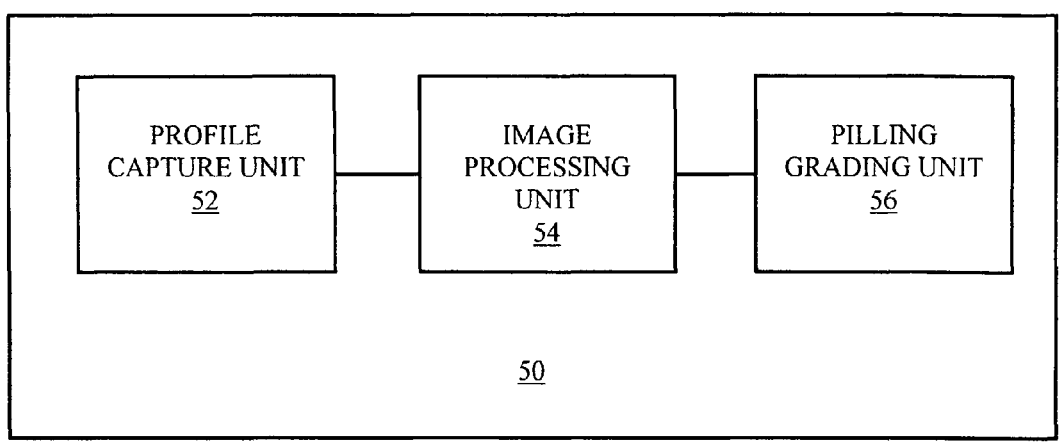
FIG. 1 illustrates the basic components of the pilling grading system.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE INVENTION

This is an invention of a method and apparatus for inspecting the surface of fabrics that have been exposed to friction and as a result may have been damaged. The damage caused is depicted by {fibers, pills, fuzziness, and snags protruding from the said surface. The assessment of the severity of the damage of fabric surface defects must take into account the size and the number of protrusions and number of other parameters of silhouettes of the fabric. The present grading system is based on a subjective comparison of the damaged fabric surface to a set of standard photographs or holograms that rank the damage from very severe (scale 1) to no damage (scale 5). It is beneficial to adjust any new method of damage evaluation or grading method to the traditional scale.

Attention is made to FIG. 1, which is schematic block diagram illustration of the structure of a grading device 50 according to embodiments of the present invention. Grading device 50 may comprise Profile Capture Unit 52 which may photograph at least several profiles of the bend in the fabric in defined increments and may transmit the data representing these profiles to mage Processing Unit 54. The output data of Image Processing Unit 54 may be fed into Pilling Grading Unit 56 that may integrate the results of the fabric surface protrusion, as received from Image Processing Unit 54, into a grading system and method, using Neural-Network (not shown in this drawing) and a parameters database to correlate the grading results of system 50 to the existing manual grading scale.

Figure 2:
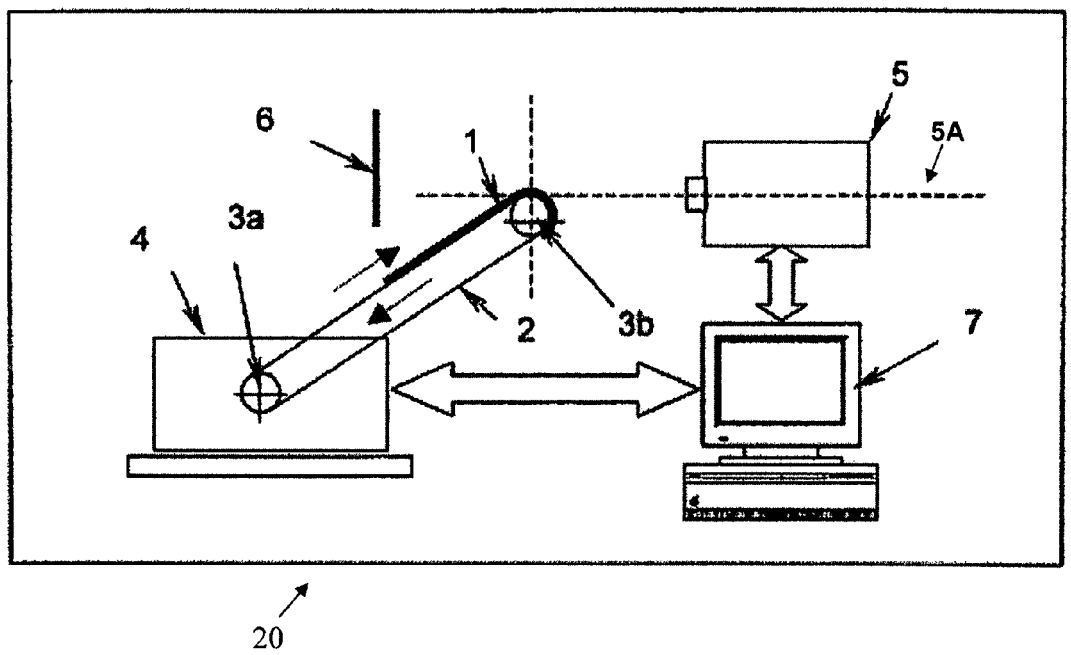
FIG. 2 illustrates the elements and the structure of the Profile Capture Unit.

Attention is made now to FIG. 2, which is a schematic illustration of a Profile Capture Unit 20, according to some embodiments of the present invention. Profile Capture Unit 20 may comprise a conveyer belt 2, which may be powered by motor 4 and may turn around its two end pulleys 3a and 3b each of about 1 cm. in diameter, a digital optical sensor 5 such as digital camera, a screen 6 placed so as to form a background of an image taken by said digital camera 6 and a computing and control unit 7, operably connectable to motor 4, background screen 6 and digital camera 5.

A strip of fabric 1 that was pre-treated to induce pilling by a standard method (such as ASTM 3512-99 or B.S. 581186 or M&S P18A or other) may be attached to conveyer belt 2 by any suitable means, such as clips (not shown in the drawing). The width of the conveyer belt may typically be 15 cms and its linear length between its two pulleys may typically be 40 cms, so as to accommodate for a standard examining strip of fabric. The conveyer belt surfaces may be placed at an angle with respect to the line of sight 5A of digital camera 5. At one of pulleys 3a or 3b may be powered motor 4, which may be a step motor that may rotate the pulley to drive belt 2 in linear increments the length of which may be controlled by computing unit 7 in the range of, for example, 0.1 to 0.5 cms.

Digital camera 5 may be placed so that its optical system is within the focal distance of the top of the fabric that has been wound onto the top pulley 3b. Screen 6 may be placed behind the top of the fabric surface with respect to digital the LOS of camera 5 and may serve as a background to the silhouette of the fabric line above the upper pulley as captured by digital camera 5. The color of the front surface of the screen that is facing the camera lens can be changed responsive to control signal received from computing unit 7 to contrast the color of tested fabric 1. If necessary, screen 6 can be translucent and the illumination of the sample would be projected on the back surface of background screen 6. Computing unit 7 may synchronize the movement of conveyer belt 2 to the exposures of digital camera 2. After each exposure and capturing of an image, the conveyer belt may be moved to forward tested fabric 1 by a preset increment. Typically a capture of an image of the silhouette of the bent fabric is taken every 2.5-5 mm along the longitudinal dimension of the tested fabric yet, other desired increments may be used. The resolution of the captured image is typically in the order of 17-20 pixels per mm (ppm).

Computing unit 7 may run an executable program able to determine and mark three different areas in the captured image: area of fabric (AF), area of protrusions (AP) and area of background (AB). According to some embodiments of the present invention these areas, as well as other characteristic features of a tested fabric, may be extracted from and/or calculated based on the images taken by Profile Capture Unit 20. Area of the fabric (AF) is considered as the bottom part of the image where the fabric is imaged. Area of the protrusions (AP) is considered the area between AF and the background, where the fabric has a substantive amount of pills, hairiness, fuzziness and like. The area of the background (AB) is the area in the image above the AP and on the sides of the AF and AP.

Figure 3:
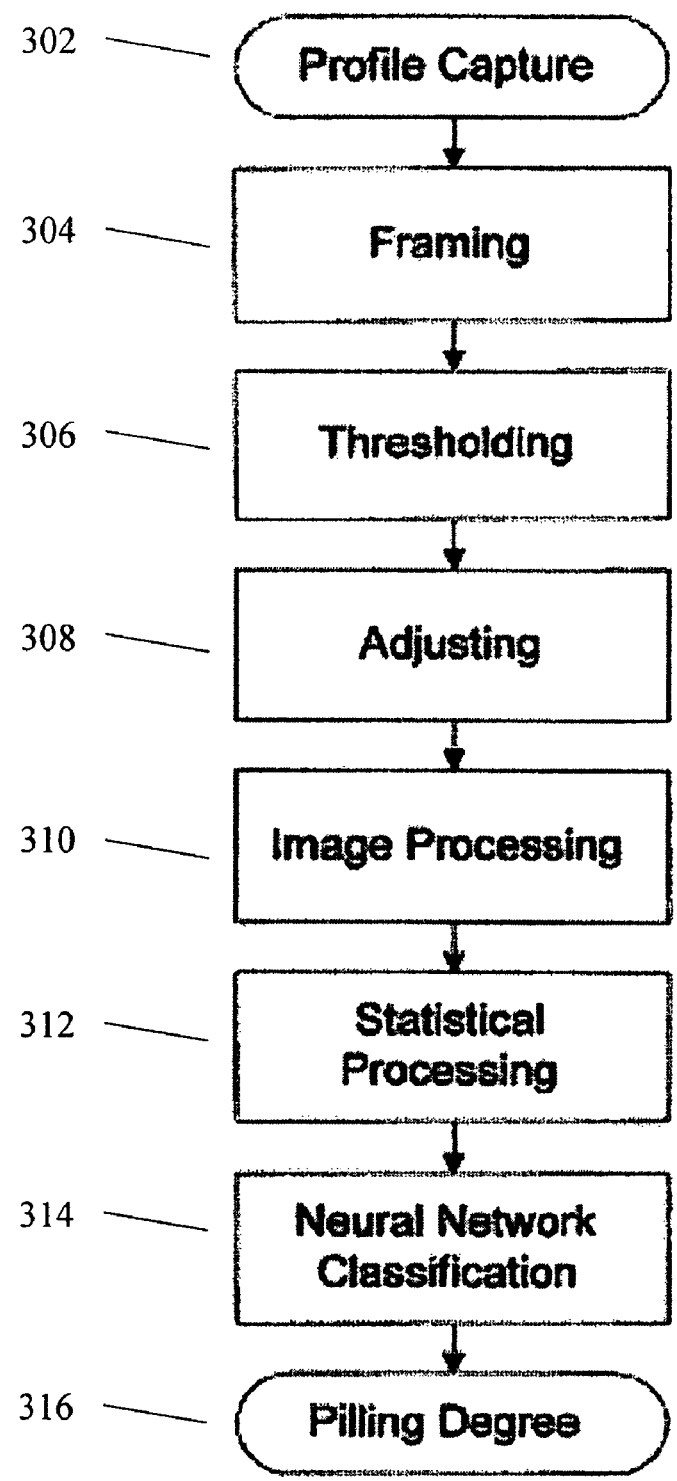
FIG. 3 is a presentation of a schematic simplified flow chart of the pilling evaluation procedure.

Attention is made now also to FIG. 3 which presents a flow chart of the pilling evaluation procedure, and to FIGS. 5A-5D which are illustrations of a grey scale image of the typical profile, a corresponding black and white image, a corresponding image on which the BL and Th lines and vertical separation lines between individual protrusions are marked and illustration of the image of the typical profile in the cross-section of fabric on the output of Profile Capture Unit 52, respectively, according to embodiments of the present invention. Profile capturing stage (block 302) and framing stage (block 304) have been described above, with respect to the detailed description of profile capture unit 20. A next stage may be Thresholding (block 306). The captured image of the tested fabric's silhouette is first transferred to Gray Scale Image where the profile is captured. The outliers are then determined. It is then transferred to Black and White Image. The area of the outliers defined in the previous step is processed by mathematical and statistical analysis to obtain a two-dimensional evaluation, as explained in more detail below. The next exposure may be analyzed in the same way but the program now may take into account the previous exposure(s) and may thus identify the protrusions that appeared in it. Sequential exposures of the fabric fold may reveal a gradual increase and then decrease in the cross-section of a protrusion located at a certain location along the silhouette image. Hence, the actual size of the protrusions, in two directions, can be determined. The data obtained from the series of exposures of the advancing folds in the fabric enables an accurate measurement of the number of protrusions, the size of the individual protrusions and their density (number per unit area of fabric). This is the essential data required for assessing damage to the fabric from protrusions such as pilling.

At this stage the operator may determine the parameters of the Image Processing program such as the number of profiles, the parameter of the average smoothness, and the threshold for the outliers. The length, height, area and the distance between the outliers for each specific profile increase as a result of the image processing. This stage is the adjusting stage (block 308).

Figure 5A:
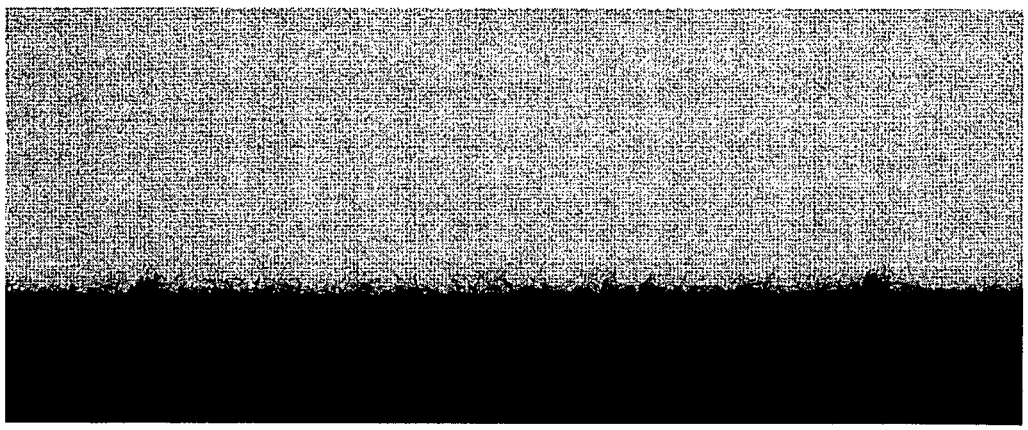
FIGS. 5A-5C illustrate a grey scale image of the typical profile, a corresponding black and white image and corresponding image on which the BL, Th lines and vertical separation lines between protrusions are marked, according to some embodiments of the present invention.
Figure 5B:
Figure 5C:
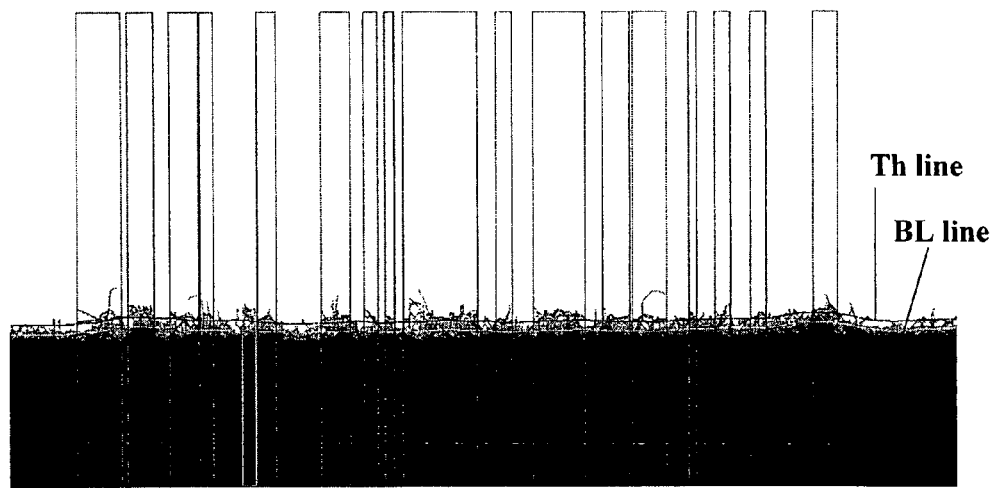
Figure 5D:
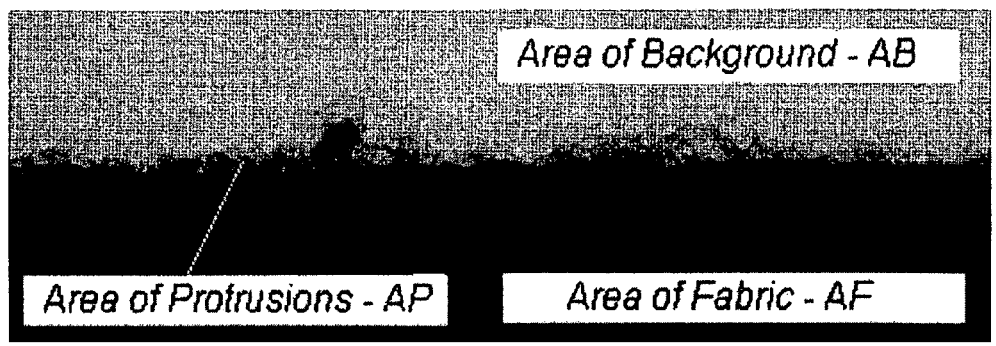
FIG. 5D illustrates the image of the typical profile in the cross-section of fabric on the output of Profile Capture Unit, according to some embodiments of the present invention.

In the image processing stage (block 310) parameters such as the number of protrusions beyond the base line (BL) and the average area of protrusion may be calculated, as will be described in details below. As shown in FIG. 5C BL and Th lines may be calculated and marked on an image of a silhouette of the tested fabric. FIG. 5D depicts the separation of the silhouette image area into AP, AF and AB areas.

The next stage is Statistical Processing (block 312). The purpose of this stage is to calculate the average values and the standard deviations for the outliers' parameters for the entire set of profiles of the fabric sample. The results of the Statistical Processing are transmitted to a Neural Network (block 314). The Neural Network has specific training data set, and can determine the pilling grading according to the existing scale, as will be detailed herein below.

Figure 4:
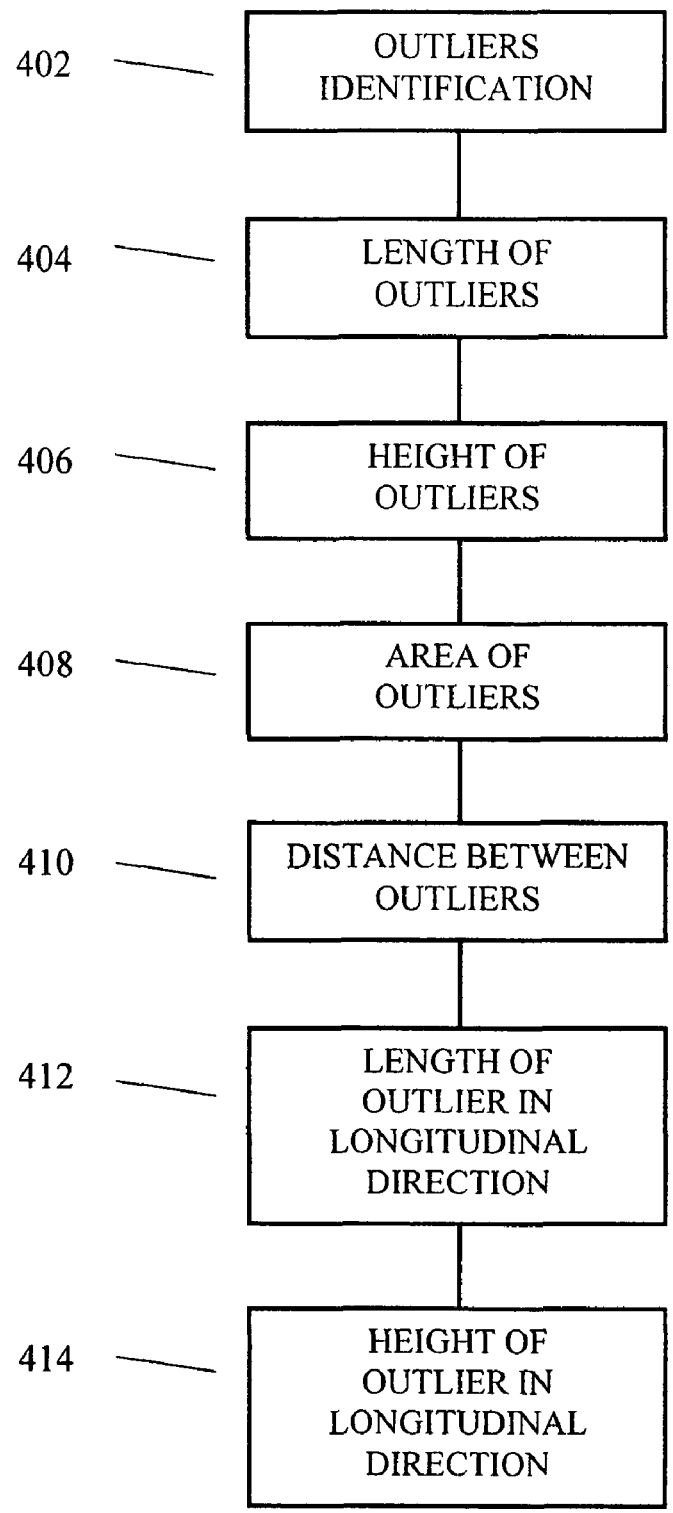
FIG. 4 is a presentation of a schematic simplified flow chart of the Image Processing Unit.

Attention is made now to FIG. 4, which describes the Image Processing stage (block 310 in FIG. 3) in some detail. This stage provides a numeric analysis of each identified outlier for each specific profile. In addition, the distance between every adjacent outlier along a profile (in the cross direction of fabric) is calculated for each specific profile. Sequential analysis of the ordered assembly of the profiles enables the program to determine the length and the height of the outliers in the longitudinal direction.

Figure 6:
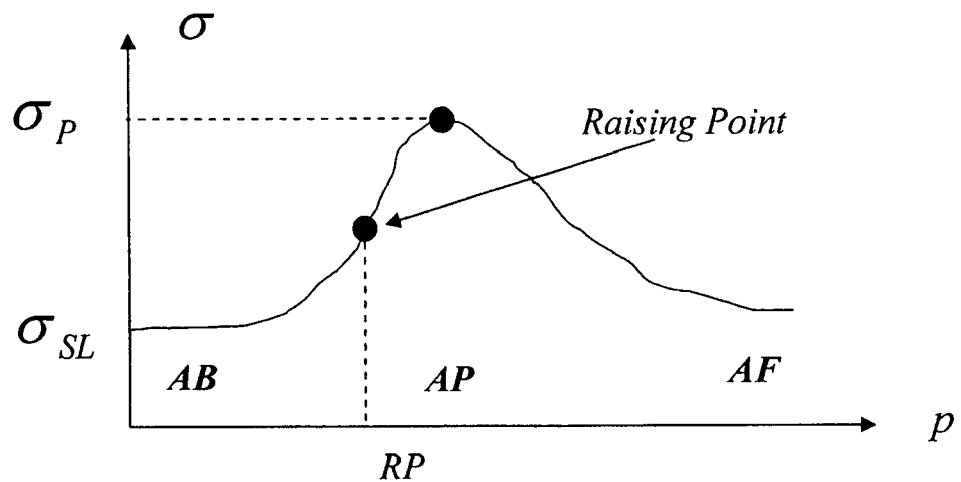
FIG. 6 illustrates a typical graph showing the changes in standard deviation of image brightness along a line substantially vertical to the fabric latitudinal line, according to some embodiments of the present invention.
Figure 7A:
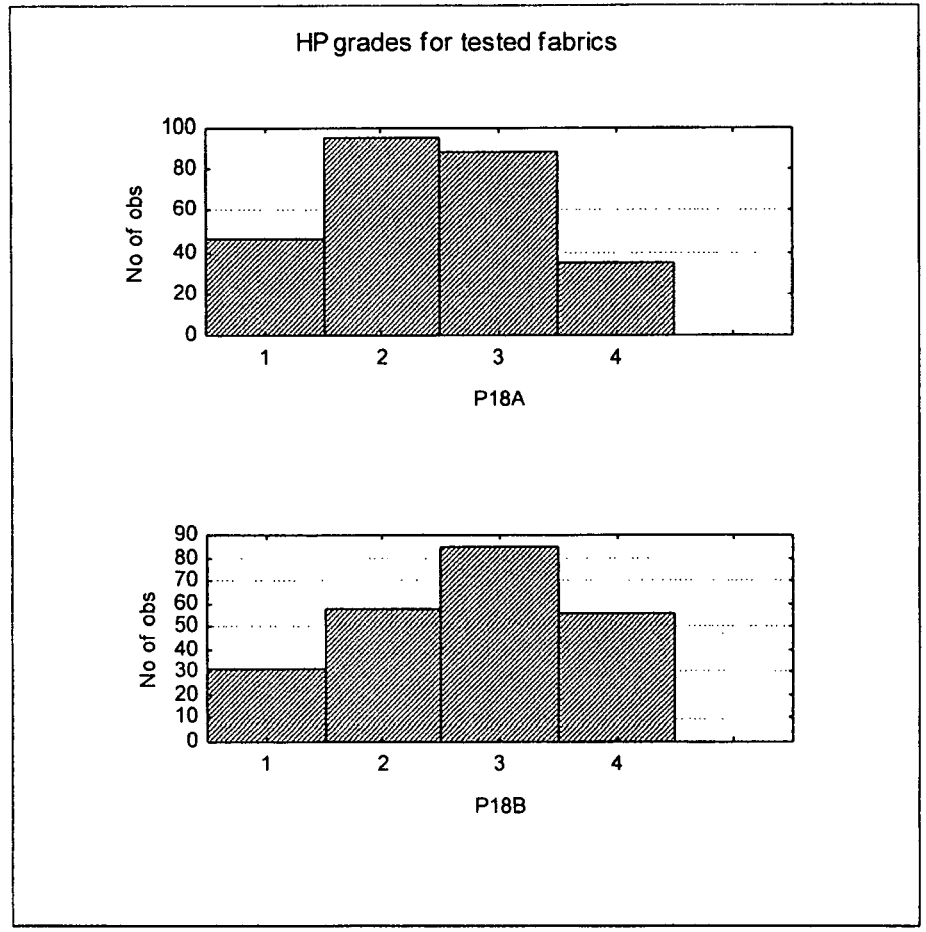
FIG. 7 illustrates the histograms of the fabric brightness and grades in the Data Set, according to some embodiments of the present invention.
Figure 7B:
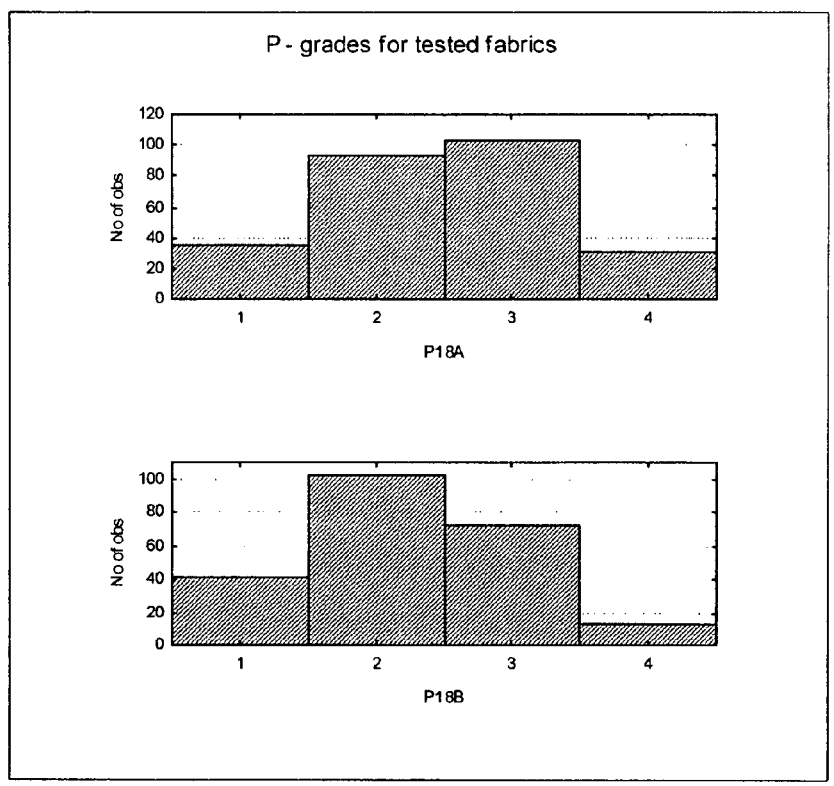
Figure 7C:
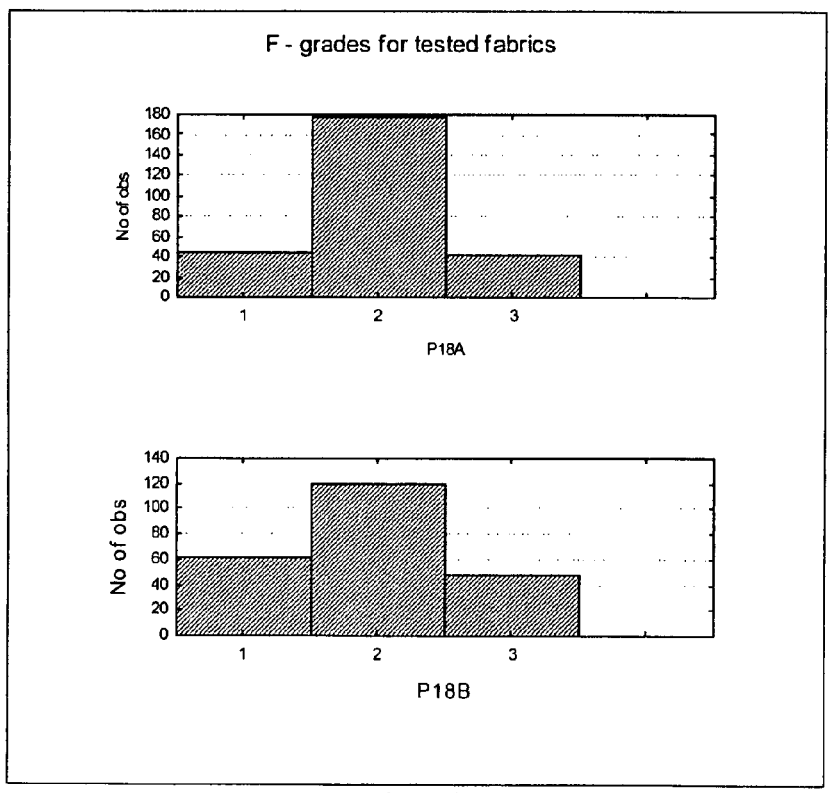
Figure 7D:
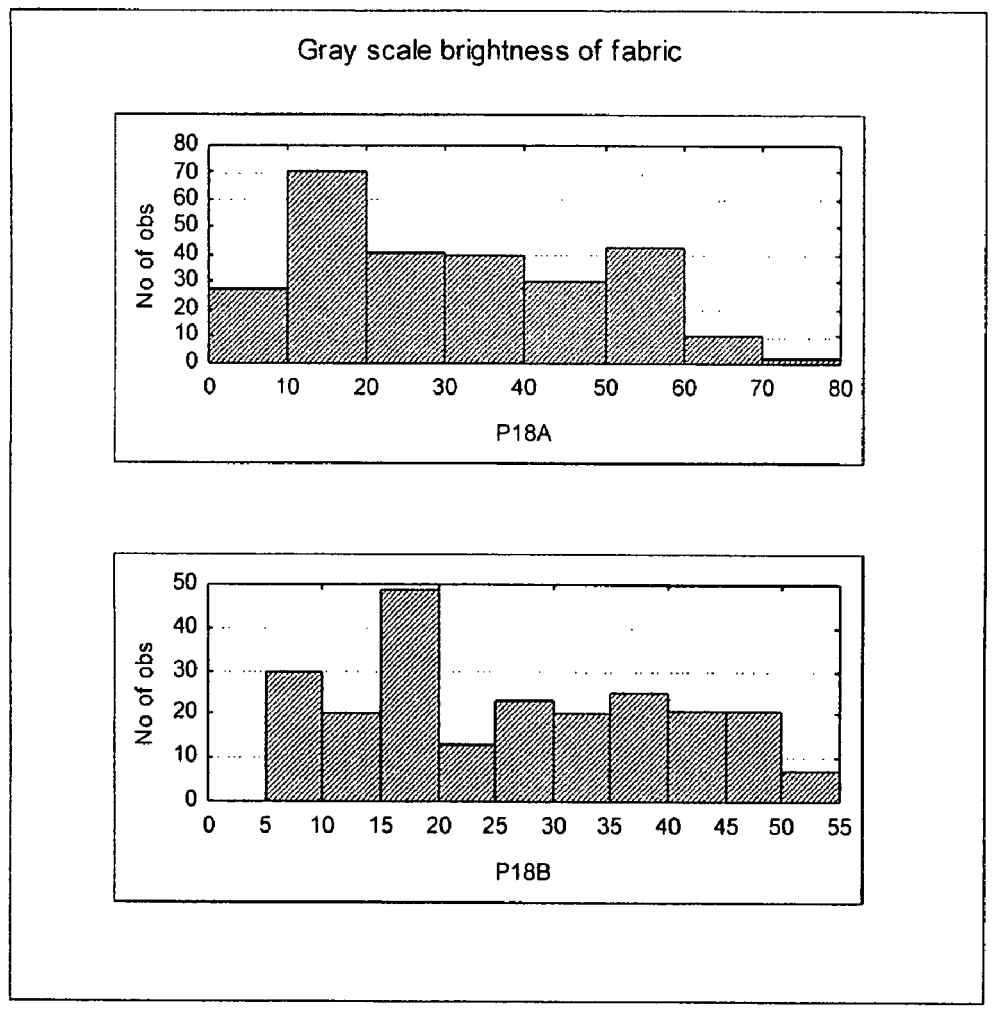

A tested fabric may substantially be uniquely characterized by a set of values given to a corresponding set of characteristic parameters. Characteristic parameters of the tested fabric may comprise:

Base Line (BL). Base Line (BL) may be defined the border line between AF and AP. Detection of the BL may be done based on analysis of the standard deviation of the brightness within a horizontal rectangle area descending from the upper end of the image and extending to the bottom line of the image, and including the zone in which the fabric is represented. When calculating the value of the standard deviation ($\sigma$) of the brightness in the upper part of the rectangle, where AB is the value of $\sigma$ is typically low. When the location inside the rectangle area approaches to the area of protrusions AP the value of $\sigma$ of the brightness significantly increases and as the location in the rectangle further approaches the bottom border line the value of $\sigma$ decreases again, as depicted in FIG. 6 to which reference is now made. FIG. 6 illustrates a typical graph showing the changes in standard deviation of image brightness along a line substantially vertical to the fabric latitudinal line, according to some embodiments of the present invention. Thus, the border line BL may be indicated as the location for each such narrow rectangle where the value of $\sigma$ reached a specific percentage, marked RP in FIG. 6, of local maximum, also indicated as a Raising Point (RP). The value of ca and the value of the image brightness at the RP point are used for the determination of the local BL location. Further to the determination of the BL, the executable program may provide for, based on the value of a and the value of the image brightness, the calculation of:

i. Alignment of the image brightness along the silhouette profile, ii. Filtration of the background for the purpose of elimination of point-noise from the background area (also called "background whitening"), iii. Moving average for the purpose of eliminating "base fluctuation" and detecting the actual border between the Protrusion Area and the Fabric Area.

Threshold (Th): The detection, calculation and indication of the location of BL and background whitening allow the separation of the AP area from the FA area. The AP area typically contains protrusions of the original fabric which are marked PF, pilling which are marked P and fuzzing which are marked F. The image of the AP area typically contains sections with P protrusions, with F protrusions and sections with separate fibers or small groups of fibers which may not be classified as P or F protrusions. The latter type of protrusions is to be eliminated from the calculations relating to characteristic parameters. This separation may be carried out based on a geometrical shape and dimensions (width and height of the image of a single protrusion) for filtering of the protrusions. For this purpose a first, geometrical Threshold (Th) may be determined so that if the geometrical features of an examined protrusion is located under the Th value that protrusion will be marked non-relevant to the analysis. The value of Th is determined during the adjustment of the image processing algorithms and the training of the Neural Networks. In order to separate P protrusions from F protrusions a value of a second threshold ($Th_{P-F}$) may be calculated. The value of the characteristic for a certain $Th_{P-F}$ of a tested fabric may be calculated, among other things, based on the fact that for a P protrusion the dimensions are, typically, higher and narrower than those of a F protrusion. Another possible method for setting a value for $Th_{P-F}$ may be based on the fact that typically the brightness (typically measured in a 1-256 grey levels) of P-protrusion is lower than that of F-protrusion. Thus, for example, for a specific fabric it may be found that protrusions with brightness level up to 20 will be marked as P and protrusions with brightness level from 21 to 35 will be marked fuzziness and protrusions with brightness level higher than 40 will not be considered at all as protrusions.

In this approach for solving separation between P-protrusion and F-protrusion the grey scale a GI index for the threshold $Th_{P-F}$ may be calculated according to the equation:

$$GI = \frac{X - F}{T_G - F} \quad 0 \le GI \le 1$$

Where:
X—protrusion brightness
F—fabric brightness
$T_G$—Grey scale threshold that is used for Baseline determination If $GI \ge T_{GI}$ the protrusion is classified as Fuzzy. Otherwise it will be classified as a Pill. $T_{GI}$ is the Grey Scale Threshold for the separation between P protrusion and F protrusion.

The border between the fabric and the background, and also the threshold line of the fabric fold—that is the line that would be seen when all surface obstacles are removed. The border between the fabric and the background may relate to the "top" line of the image of a silhouette and to the side lines of same. Parameters that can be extracted from the top line of the image of the silhouette are an average height of the top line and its standard deviation. Use of these parameters may assist in determining border line in accuracy of up to −/+1 pixel. Once the border line for a silhouette is determined computing unit 7 may further perform cropping process to 'remove' portions of the image extending out of the border line.

The decision of the position of the threshold line is also based on the average height of the silhouette. The software processes any protrusion above the threshold line.

Additional characteristic parameters: In order to facilitate automated grading of a fabric the apparatus and method according to the present invention may use additional characteristic parameters, which may be extracted from the silhouette image or calculated based on extracted or calculated parameters. Such additional parameters may comprise:

C—The number of protrusions beyond the baseline
W—Protrusion width
H—Protrusion height
A—Protrusion area
S—Standard deviation of the distance between protrusions
B—Fabric brightness Parameters C, W, H, A and S may be determined as an ensemble average. The vector of protrusion parameters $\vec{P}_P$ is given by the formula:

$$\vec{P}_P = [C, W, H, A, S, B]^T$$

Hairiness, hairiness area: According to an embodiment of the present invention the apparatus and method of the present invention may be used to estimate the height and the average brightness of the hairiness area AH. The average value of the Base Line BL, that is the average value of the height of the base line above a reference horizontal line across the width of the sample fabric, may be used as the lower border ($i_B$) of the AH area. The upper border ($i_U$) of the AH area may be determined by calculating the standard deviation of brightness of the rows close to the border between AB and AP:

$$\sigma(i) = \left( \frac{1}{N} \sum_{j=1}^{N} (B(i,j) - \overline{B}(i,j))^2 \right)^{1/2}, \; i = \overline{1, M}$$

Once the value of σ(i) is calculated, it may be compared to threshold $(1+T_H)\sigma_{SL}$:

$$\Delta(i) = \sigma(i) - (1+T_H)\sigma_{SL}, i=\overline{1,M}$$

The $i_U$ row where Δ(i) becomes nonnegative may be used to determine the upper border of the AH area. The height, as measured vertically with respect to a latitudinal line may then be given by:

$$H_H = (i_r - i_B)$$

The average brightness of the AH area may be calculated by formula:

$$\overline{B}_H = \frac{1}{N} \sum_{j=1}^{N} \frac{1}{M - BL(j)} \sum_{i=i_H}^{M-BL(j)} B(i,j)$$

The hairiness index ($I_H$) may be determined as a linear convolution of the height and average brightness of the AH area:

$$I_H = \alpha \cdot \frac{\overline{B}_H}{F} + (1-\alpha) \cdot \frac{H_H}{L}, \; 0 \leq I_H \leq 1,$$

where:

L—normalization factor

F—fabric brightness

The conversion of the Hairiness grading into the expert grading scale can be produced by the division of the definition range of the $I_H$ index into five subintervals:

$G_H=1$, if $I_{H1} \leq I_H$, $G_H=2$, if $I_{H2} \leq I_H < I_{H1}$, $G_H=3$, if $I_{H3} \leq I_H < I_{H2}$, $G_H=4$, if $I_{H4} \leq I_H < I_{H3}$, $G_H=5$, if $I_H < I_{H4}$.

The index of hairiness value of the $I_H$, that determines the limits of the subintervals, must be selected so that the probability of differences between the expert grade of hairiness and the grade determined according to the present invention do not exceed a permissible value.

Snag Detection: Snag (S) detection has some specific properties and it differs from Pills (P) and Fuzzy (F) detection. The main difference is that the dimensions (scale) of Snags as a rule are much bigger than the dimensions of Pills and Fuzzy. As a result of this, errors of the baseline determination and geometrical parameters of protrusions have a weak influence on the accuracy of S-grading. Another difference is that the Snag is a singular effect and is not mixed with Pills, Fuzzy and Hairiness effects. Thus there is no need to separate different types of protrusions when detecting Snags. Furthermore, according to Marks & Spencer P21A Test Method Snagging grading relates to the tested specimens only since there are no snags in the original fabric. As a result of this, the algorithm for snagging evaluation may represent a simplified modification of the HP, P, and F algorithm. The S-algorithm is based on two parameters that are obtained at the Image Processing phase of a set of profile images:

1. Number of protrusions beyond the baseline—C
2. Average area of protrusion—A

Snagging Index ($I_s$) is determined as a linear convolution of these two parameters:

$$I_S = \alpha \cdot C + (1-\alpha) \cdot A$$

This Snagging Index is the basis for the snagging grading analogous to H grading on the basis oh Hairiness Index:

$G_S=1$, if $I_{s1} \leq I_S$ $G_S=2$, if $I_{S2} \leq I_S < I_{S1}$ $G_S=3$, if $I_{S3} \leq I_S < I_{S2}$ $G_S=4$, if $0 < I_S < I_{S3}$ $G_S=5$, if $I_S=0$ The limits of the subintervals $I_{Si}$, i=1, 2, 3 are determined as a result of a comparison analysis of the expert grades and the parameters obtained by Image Processing. The algorithm for grading of snag length is built in the same manner. Statistical analysis of the results of for the sample of 38 woven and single knitted fabrics, showed that the length and area of snags have a very high correlation. However, taking into account that the calculation of the snag area is simpler than the calculation of the snag length, the snag area has been used for the estimation of the snag length. A three-level scale is used for the snag length grading: S—short, M—medium, and L—long. The algorithm for grading of snag length according to the present invention in an expert scale is as follows

TABLE 1

| Fabric Code | Revolutions | Specimen | Expert Grades | | |
|---|---|---|---|---|---|
| | | | HP | P | F |
| kp-34 | 0 | Original | 4 | | |
| | 800 | Tested | 1 | 1 | 1 |
| | | | 1 | 1 | 1 |
| | | | 2 | 1 | 2 |
| | | | 1 | 1 | 1 |

Table 2 below presents an example of a part of the Data Set with fabric brightness—B and protrusion parameters:

TABLE 2

| | Pilling | | | | | Fuzziness | | | | | General | | | | |
|---|---|---|---|---|---|---|---|---|---|---|---|---|---|---|---|
| B | P_C | P_W | P_H | P_A | P_D | F_C | F_W | F_H | F_A | F_D | G_C | G_W | G_H | G_A | G_D |
| 27 | 0 | 0 | 0 | 0 | 0 | 1.56 | 0.71 | 0.37 | 0.12 | 0.13 | 1.56 | 0.71 | 0.37 | 0.12 | 0.13 |
| 25 | 1.6 | 1.21 | 0.48 | 0.39 | 0.16 | 9.99 | 1.52 | 0.54 | 0.33 | 0.8 | 11.59 | 1.53 | 0.56 | 0.35 | 0.83 |
| 26 | 1.67 | 1.42 | 0.36 | 0.34 | 0.13 | 9.15 | 1.56 | 0.56 | 0.33 | 0.76 | 10.82 | 1.63 | 0.55 | 0.36 | 0.8 |
| 37 | 3.85 | 1.68 | 0.57 | 0.49 | 0.38 | 6.36 | 1.68 | 0.5 | 0.3 | 0.63 | 10.21 | 1.73 | 0.55 | 0.39 | 0.74 |
| 36 | 2.38 | 1.57 | 0.63 | 0.47 | 0.21 | 8.64 | 1.39 | 0.53 | 0.29 | 0.76 | 11.02 | 1.45 | 0.55 | 0.33 | 0.81 |

$G_L = L$, if $A \geq A_L$ $G_L = M$, if $A_S \leq A < A_L$ $G_L = S$ if $A < A_S$ Grading of a tested fabric according to embodiments of the present invention may need a new approach towards the computing platform that is required. Grading is an estimation of grade—G (it can be P grade $G_P$, F grade $G_F$, or HP grade $G_{HP}$) in accordance to the results of Image Processing phase, according to the formula:

$$G = A(P_P),$$

Where: A is the grading operator

For the HP, P, and F grading the operator A can be calculated by a Neural Network computing platform. The Neural Network may implement a convolution of the parameters obtained in the Image Processing phase to the required grade—G. To construct and train the Neural Network it may be necessary to prepare a Data Set that may contain the parameters of protrusions (vector $P_P$) and the expert grades for a sufficient representative sample of fabrics. When preparing the Data Set it is beneficial to achieve a uniform representation of all grades and all the different color shades (dark, medium, and light). It is evident that the Data Set should be built up from a homogeneous group of fabrics. For example, it can be a group of single knitted fabric (Marks & Spencer, P18A Test Method—Random Pilling Drum) or a group of knitwear (Marks & Spencer, P18B Test Method—Random Pilling Drum—Reverse Action).

Table 1 below presents an example of a part of the Data Set with test specification and expert grades for a specific fabric Where:

P_C, F_C, G_C are the average number of pills, fuzziness, and the sum, respectively.

P_W, F_W, G_W are the average width of protrusions P, F and G, respectively,

P_H, F_H, G_H are the average height of protrusions P, F and G, respectively,

P_D, F-D, G_D are the standard deviation of the distances between protrusions P, F and G, respectively.

The preparation of the Data Set according to the present invention should be carried out so as to ensure a uniform distribution of all levels of grades. Prior to this the grades are unknown from a corresponding testing session made by a traditional human expert and the sampling for the Data Set takes place after the physical testing and expert grading. FIGS. 7A-7D present sample histograms for HP, P, and F grades and for fabric brightness, respectively, obtained for the Marks & Spencer M&S P18A and P18B Test Methods. Amongst these sample histograms the only the histogram for fabric brightness—B may be considered as uniform. This is quite usual as the sample for fabric brightness is determined before physical testing phase. The neural network that has been built and trained, for example, on the base of the F-grade histogram for Marks & Spencer P18A Test Method, is oriented to grade $G_F = 2$ and demonstrates the best correlation to the expert grades for the grades $G_F = 1$ or $G_F = 3$. On the other hand, these histograms can show the actual proportion between the different levels of the HP, P, and F grades. Based on this, the histograms shown in FIGS. 7A-7D have been used for building and training the neural network for grading.

Figure 8:
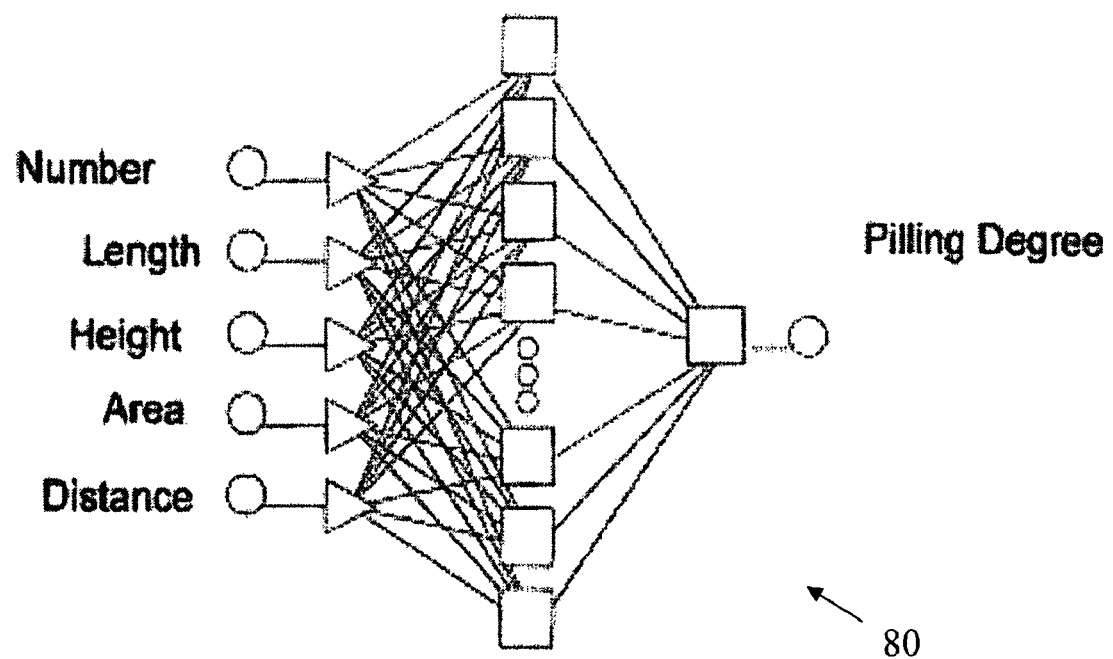
FIG. 8 illustrates the structure of the Neural Network for pilling grading, according to some embodiments of the present invention.

Attention is made now to FIG. 8, which illustrates a structure of a Neural Network computation platform 80 for pilling grading. The Neural Network computation platform 80 may perform the computations involved in matching manual grading to the set of calculated parameters of a tested fabric. The grading of the surface evaluation of textile fabrics on the base of the vector $P_P$ is a classification issue. One of the most effective approaches to carry out this kind of classification may be done with Neural Network computation platform 80. An interpretation of a Neural Network computation platform 80 output is an estimate of probability of grade, in which case the network actually learns matching of human-grade to a set of parameters which represent a tested fabric. The mission of building and training a Neural Network can be formulated, according to embodiments of the present invention, as the mission of estimation of a probability density function of the human-grades. If an approximation of the probability density function is performed by kernel-based approximation the Neural Network belongs to the category of Probabilistic Neural Networks (PNN). The only control factor that needs to be selected for probabilistic neural network training is the smoothing factor. An appropriate figure is chosen by experiment, by selecting a number that produces a low selection error, because PNNs are not overly sensitive to the precise choice of smoothing factor. The greatest advantages of PNNs are the training speed and the fact that the output is probabilistic. Training a PNN may consist in the main part of copying training cases into the network, and so is as close to instantaneous as can be expected. On the basis of obtained Data Set it is necessary to construct a specific PNN for each type of grade: HP, P, and F grade.

The selection criterion for PNN is very important from the practical point of view. The PNN that is constructed for a specific Data Set is distinguishing by its kernel-function only. The training of the PNN consists of the generation of a great number of networks with a different value of this parameter. The selection criterion can be based on the quality of classification but not on the value of the parameter of the kernel-function. The quality of classification (grading) for each level of the grade is determined by the percentage of coincidence between the expert and PNN grades. The selection criterion can be presented by linear convolution:

$$Q = \sum_{i=1}^{5} \alpha_i \cdot Q_i, \sum_{i=1}^{5} \alpha_i = 1,$$

where:

$Q_i$—percentage of coincidence between the expert and PNN grades for the i-level of grade $\alpha_i$—weighting factor (priority) for the i-level of grade.

If $\alpha_i=0.2$ for $i=\overline{1,5}$ the selection criterion enables the PNN with the highest total percentage of the coincidence grades to be chosen.

The problem of PNN training is to search for the network that provides the highest value of grading quality—max Q for the given values of the weighting factor—$\alpha_i$, $i=\overline{1,5}$. Table 3 presents the percentage of coincidence grades for the PNN for HP-tested fabric (M&S P18B Test Method). Table 3 contains the data for the best for the consecution neural networks. The network-68 is the best network for the selection criteria $Q_{1234}$ ($\alpha_1=\alpha_2=\alpha_3=\alpha_4=0.25$), $Q_{123}$ ($\alpha_1=\alpha_2=\alpha_3=0.33$), and $Q_{12}$ ($\alpha_1=\alpha_2=0.50$). If the criterion $Q_{23}$ ($\alpha_2=\alpha_3=0.50$) is used for the election, the network-56 is the best network.

TABLE 3

Percentage of coincidence between Expert and PNN grades

| Number of PNN | Grades | | | | $Q_{1234}$ | $Q_{12}$ | $Q_{23}$ | $Q_{123}$ |
| | 1 | 2 | 3 | 4 | | | | |
| --- | --- | --- | --- | --- | --- | --- | --- | --- |
| 2 | 58 | 76 | 59 | 86 | 279 | 134 | 135 | 193 |
| 22 | 45 | 86 | 69 | 54 | 254 | 131 | 155 | 200 |
| 48 | 45 | 76 | 77 | 53 | 251 | 121 | 153 | 198 |
| 52 | 58 | 76 | 78 | 53 | 265 | 134 | 154 | 212 |
| 56 | 45 | 86 | 75 | 67 | 273 | 131 | 161 | 206 |
| 61 | 61 | 71 | 82 | 46 | 260 | 132 | 153 | 214 |
| 68 | 65 | 81 | 76 | 67 | 289 | 146 | 157 | 222 |

Figure 9:
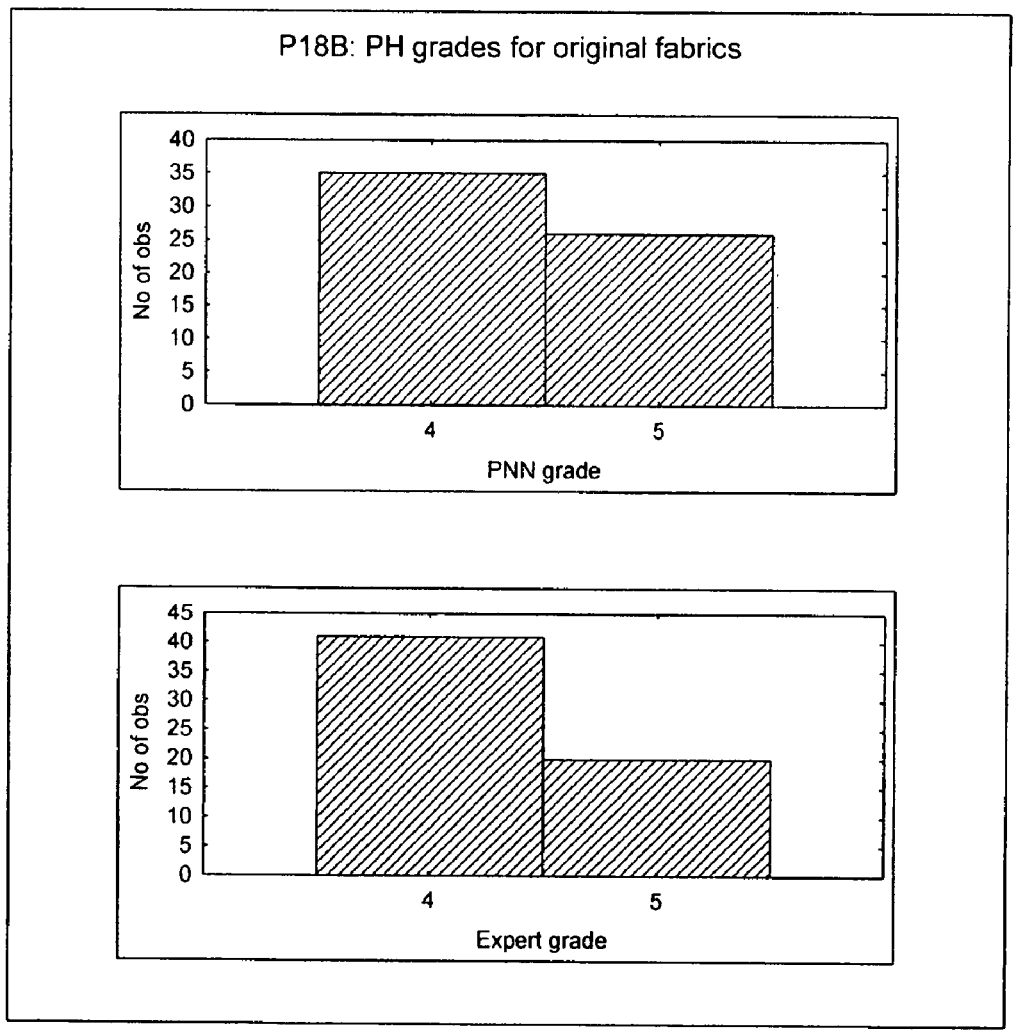
FIG. 9 illustrates the histogram for HP grades for an original fabric obtained by expert and neural network, according to some embodiments of the present invention.
Figure 10:
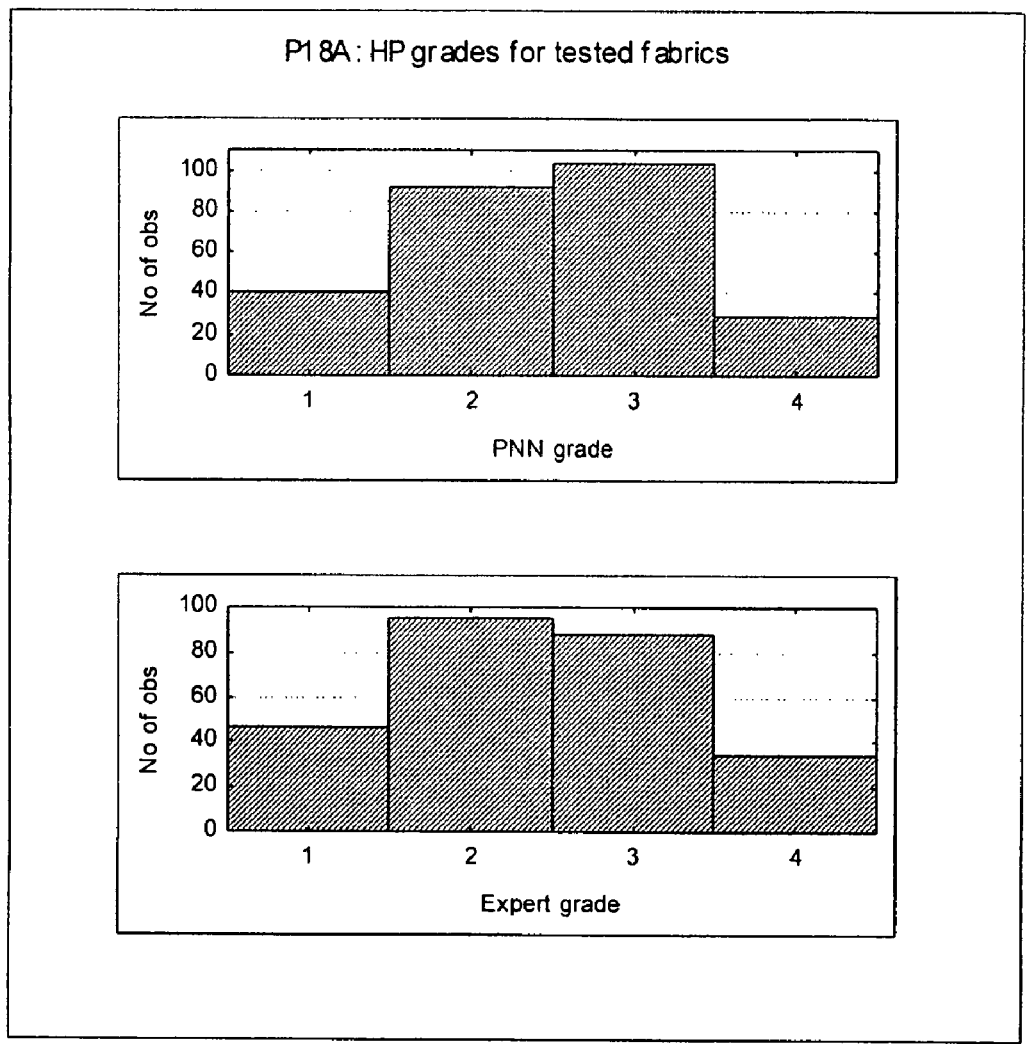
FIG. 10 illustrates the histogram for HP grades for tested fabric obtained by expert and neural network for M&S P18A Test Method, according to embodiments of the present invention.
Figure 11:
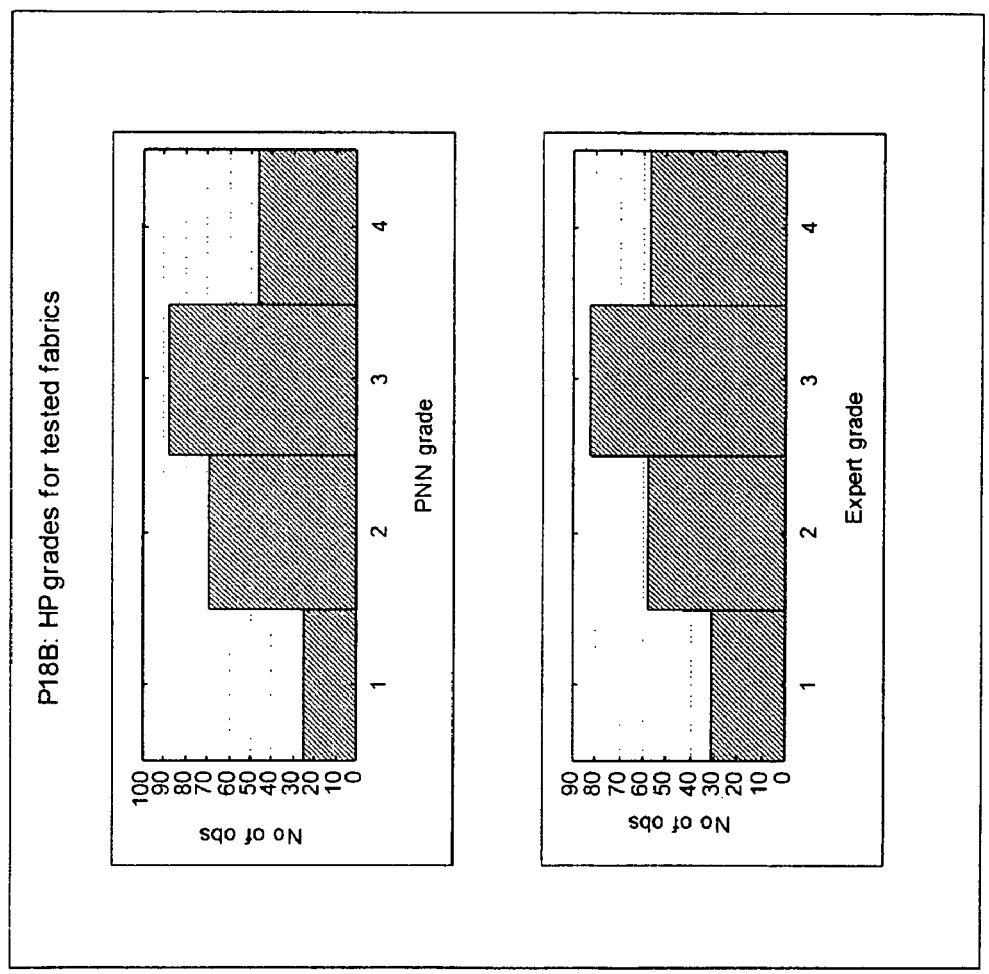
FIG. 11 illustrates the histogram for HP grades for tested fabric obtained by expert and neural network for M&S P18B Test Method, according to embodiments of the present invention.

Attention is made now to FIGS. 9, 10 and 11 which illustrate the histogram for HP grades for an original fabric (according to M&S P18B Test Method) obtained by experts and the network of the present invention (marked PNN), histograms for HP grades for the tested fabric for M&S P18A and P18B Test Methods respectively. All histograms indicate very similar distributions of the expert and PNN grades for the HP grades.

Hairiness and Snagging Grading: As was shown above, H grading is based on the calculation of the Hairiness Index—$I_H$ and the estimation of membership to one of five subintervals of this index. For this approach it is necessary to determine the parameter of linear convolution—$\alpha$ and the limits of subintervals $I_{H_i}$ for $i=\overline{1,4}$. A special Data Set of 41 different fabrics was prepared for this. The Data Set contains averaged grades of three experts for original fabrics. Parameter of the linear convolution and the limits of subintervals were determined by using a search method. Minimum of the average value of absolute difference between the expert H grade and the calculated H grade was used as a criterion of this search method. The following values of the H-grading algorithm were obtained: $\alpha=0.1$; $I_{H1}=0.52$; $I_{H2}=0.47$; $I_{H3}=0.35$; $I_{H4}=0.30$. Minimum of the absolute difference between the expert H-grade and the calculated H-grade is equal to 0.53. It should be noted that this result was obtained on the basis of subjective expert grades. The experts used an imaginary scale of H-grades. This scale was not based on pictures/holograms or any other specification of the H-grading procedure or rules.

A Data Set of 38 woven and single knitted fabrics was used for estimating the parameters of S grading algorithms: $\alpha$, $I_{S1}$, $I_{S2}$, $I_{S3}$, $A_L$, and $A_S$. As a result of the minimization of the absolute difference between the Expert and SET-machine grades for snagging and length of snags, the following values of parameters were obtained: $\alpha=0.6$, $I_{S1}=10.6$, $I_{S2}=5.8$, $I_{S3}=3.8$, $A_L=2.5$, $A_S=1$.

Test results: Comparative analysis of the expert and elaborated device grades is the main goal of the testing. The testing includes two stages: testing of correlation between expert and machine grades and testing of repeatability of the machine grades. The correlation test consists of comparison of the expert and machine grades for the following cases:

1. HP grade for one specimen of the original fabric
2. Average HP grade for four specimens of the tested fabric
3. Average P grade for four specimens of the tested fabric
4. Average F grade for four specimens of the tested fabric The repeatability test consists of a comparison of HP, P, and F grades for a series of tests for the same specimen under the same conditions. The repeatability was estimated for the cycle average of four consecutive grades within the series.

Marks and Spencer M&S P18A Test Method: This test method is designated for single knitted fabric. The total number of the tested fabrics is 27. Tables 4-6 present the results of statistical analysis for HP-, P-, and F-grades.

TABLE 4

Hologram/Picture grades

| Difference Interval | Number of cases | Percentage | Grouped Percentage |
|---|---|---|---|
| 0 <= difference <= 0.5 | 18 | 67 | 93 |
| 0.5 < difference <= 1 | 7 | 26 | |
| 1 < difference | 2 | 7 | 7 |

TABLE 5

Pilling grades

| Difference Interval | Number of cases | Percentage | Grouped Percentage |
|---|---|---|---|
| 0 <= difference <= 0.5 | 7 | 37 | 74 |
| 0.5 < difference <= 1 | 7 | 37 | |
| 1 < difference | 5 | 26 | 26 |

TABLE 6

Fuzzing grades

| Difference Interval | Number of cases | Percentage | Grouped Percentage |
|---|---|---|---|
| 0 <= difference <= 0.5 | 13 | 62 | 100 |
| 0.5 < difference <= 1 | 8 | 38 | |
| 1 < difference | 0 | 0 | 0 |

Results of the repeatability test are as follows: 100% for HP-grade, 91% for P-grade, and 100% for F-grade.

Marks and Spencer M&S P18B Test Method: This test method is designated for knitwear. The total number of tested fabrics is 60. Tables 7-9 present the results of statistical analysis for HP, P, and F-grades.

TABLE 7

Hologram/Picture grades

| Difference Interval | Number of cases | Percentage | Grouped Percentage |
|---|---|---|---|
| 0 <= difference <= 0.5 | 15 | 75 | 100 |
| 0.5 < difference <= 1 | 5 | 25 | |
| 1 < difference | 0 | 0 | 0 |

TABLE 8

Pilling grades

| Difference Interval | Number of cases | Percentage | Grouped Percentage |
|---|---|---|---|
| 0 <= difference <= 0.5 | 17 | 85 | 100 |
| 0.5 < difference <= 1 | 3 | 15 | |
| 1 < difference | 0 | 0 | 0 |

TABLE 9

Fuzzing grades:

| Difference Interval | Number of cases | Percentage | Grouped Percentage |
|---|---|---|---|
| 0 <= difference <= 0.5 | 17 | 85 | 100 |
| 0.5 < difference <= 1 | 3 | 15 | |
| 1 < difference | 0 | 0 | 0 |

The results of the repeatability test for M&S P18B Test Method are as follows: 100% for HP grade, 100% for P grade, and 87% for F grade.

Hairiness Grading: This test method is designated for single knitted fabric. The total number of tested fabrics is 41. Table 10 presents the results of statistical analysis for Hairiness:

TABLE 10

| Difference Interval | Number of cases | Percentage | Grouped Percentage | |
|---|---|---|---|---|
| 0 | 13 | 32 | 64 | 98 |
| 0 < difference <= 0.5 | 13 | 32 | | |
| 0.5 < difference <= 1 | 14 | 34 | 34 | |
| 1 < difference | 1 | 2 | 2 | 2 |

The repeatability test shows 100% coincidence for the Hairiness grading. The grades of two independent experts are the same in 66% of the tests. This percentage can be interpreted as a repeatability index for the expert grading of hairiness. Attention is made also to FIG. 12 which presents typical fabric images with the upper and lower limits of the hairiness that were obtained by Image Processing.

Snagging Grading: Table 11 presents results of testing for Snagging:

TABLE 11

| Difference I | Number of cases | Percentage | Grouped Percentage |
|---|---|---|---|
| 0 | 27 | 71 | 97 |
| 0.5 | 10 | 26 | |
| 1 | 1 | 3 | 3 |
| Total | 38 | 100 | 100 |

Repeatability test for snagging was carried out on samples of four fabrics with a different S grade. The number of tests for each fabric was 5. The test results show 100% level for the Repeatability Index of every fabric.

We have described a new approach to objective evaluation for all types of textiles surface defects: pilling, fuzziness, snagging, and hairiness. We present a new method of protrusion capturing, algorithms of the image processing for the protrusions parameterization, and the grading procedures are based on the neural networks for pilling and fuzziness or the thresholds for snagging and hairiness. The testing results show the ability of the approach and the elaborated equipment to produce high level reliable and consistent grades for all above mentioned tests of textiles surface quality. The obtained results allow elimination errors due to the subjective human grading procedure and provide objective textile surface grades according to the existing standards The average value of the outliers' parameters for the entire set of profiles of the fabric sample represents the 5-D input of the network. The output of this Neural Network is the value of pilling degree corresponding to a specific set of outlier parameters. The network is designed and trained on the data set. The data set was obtained by expert estimations of the fabric's pilling according to the requirements of ASTM D 3512-96 Standard Test Method for Pilling Resistance and Other Related Surface Changes of Textile Fabrics: Random Tumble Pilling Tester.

In various embodiments of the invention:

A method for the detection of fabric surface and surface protrusions and for the classification of fabric quality according to the geometrical parameters and population density thereof, said method comprising the steps a. providing a sample of the textile to be classified;

b. bending said sample over a small diameter element;

c. generating a set-off two-dimensional image of the portion of the fabric sample being bent;

d. advancing said fabric sample by a small increment;

e. repeating steps c and d as often as necessary to scan said fabric sample;

f. counting the number of protrusions;

g. measuring and calculating the geometrical parameters of each protrusion;

h. calculating the degree or degrade of said protrusions by means of a neural network; and The invention may further include the above mechanism wherein the fabric folding is accomplished by a rotating or stationary tube.

The invention may further include the folding mechanism wherein the fabric is folded over a stationary or moving edge.

The invention may further include a detection device wherein any electro-optical device is used for capturing the image of the protrusion silhouette and transfers it to the processor.

The invention may further include that in the background screen the color of its surface seen by the detection device, can be changed.

The invention may further include that the said background screen comprises the opacity or the translucency of the screen can be changed to enhance the contrast of the protrusion silhouette as seen by the detection device.

The invention may further include the method and apparatus for the detection of fabric surface protrusions as described wherein illumination is added to enhance the image captured by the detection device.

The invention may further include the method and apparatus for the detection of fabric surface protrusions as described wherein, the system can calculate the number of protrusions for a tested sample of fabric.

The invention may further include the method and apparatus for the detection of fabric surface protrusions as described wherein the system can calculate the three-dimensional size of the protrusions for a tested sample of fabric.

The invention may further include the method and apparatus for the detection of fabric surface protrusions as described wherein the protrusions are the result of pilling of a fabric surface.

The invention may further include the method and apparatus for the detection fabric surface protrusions as described wherein the parameters of protrusions are processed by a Neural-Network for pilling grading.

The invention may further include the method and apparatus for the detection of fabric surface protrusions wherein the protrusions are the result of hairiness of a fabric surface.

The invention may further include the method and apparatus for the detection fabric of surface protrusions wherein the protrusions are the result of foreign bodies on a fabric surface.

The invention may further include the method and apparatus for the detection fabric of surface protrusions as described wherein the protrusions are apparent on any pliable surface.

The invention claimed is:

1. A method performed by a processor for evaluating a fabric, the method comprising:
    capturing an image of profile of said fabric;
    processing the image to obtain dimensional and quantitative characteristics of outliers of said fabric;
    calculating statistical parameters of protrusions in said outliers; and
    grading the fabric based on said calculated statistical parameters by a neural network computation platform,
    wherein said grading comprises selection by said neural network computation platform a grade determined by a probabilistic neural network having a highest value of grading quality according to a selection criteria, the selection criteria based on a coincidence between a data set of expert grades and grades given by said probabilistic neural network during a training process of said probabilistic neural network.

2. The method according to claim 1, said processing comprising:
    determining a first border line between an area of the fabric and an area of protrusions out of said fabric; and
    determining a second border line between the area of protrusions and a background of said image.

3. The method according to claim 2, said processing further comprising distinguishing between pilling protrusions and fuzzy protrusions in said area of protrusions under said second border and above a determined first threshold below said second border.

4. The method according to claim 3, wherein said distinguishing between pilling protrusions and fuzzy protrusions is based on at least a determined second threshold in a parameter from a list comprising height of protrusion, width of protrusion and brightness of protrusion.

5. The method according to claim 2, said processing further comprising obtaining a vector of protrusions parameters for at least one of pilling protrusions and fuzzy protrusions, the parameters including at least one of a list comprising number of protrusions beyond said first border line, protrusion width, protrusion height, protrusion area, standard deviation of the distance between protrusions and fabric brightness.

6. The method according to claim 5, wherein said grading comprises at least one of pilling protrusions grading and fuzzy protrusions grading, and is based on said vector of protrusions parameters.

7. The method according to claim 2, wherein said processing comprises determining height and average brightness of a hairiness area.

8. The method according to claim 7, wherein a lower border of said hairiness area is determined based on an average height of said first border line.

9. The method according to claim 7, wherein an upper border of said hairiness area is determined based on a threshold of a change in a standard deviation of brightness.

10. The method according to claim 2, wherein said processing comprises snag detection.

11. The method according to claim 2, wherein the first border line is determined based on standard deviation of brightness of the image in a region from an upper end of the image to a bottom end of the image.

12. The method according to claim 11, wherein the first border line is set where the standard deviation of brightness reaches a specific percentage of a local maximum.

13. The method according to claim 2, wherein the first border line is determined based on brightness of the image.

14. The method according to claim 1, wherein said grading comprises grading hairiness of said fabric based on a hairiness index dependent on height and average brightness of a hairiness area.

15. The method according to claim 1, wherein said grading comprises grading of snagging of said fabric based on a snagging index dependent on number of snags and average area of the snags.

16. An apparatus for evaluating a fabric, the apparatus comprising:
　　an image capturing unit to capture an image of profile of said fabric;
　　a computing unit to process the image to obtain dimensional and quantitative characteristics of outliers of said fabric and to calculate statistical parameters of protrusions in said outliers; and
　　a neural network computation platform to grade the fabric based on said calculated statistical parameters,
　　wherein said neural network computation platform is to select a grade determined by a probabilistic neural network as having a highest value of grading quality according to a selection criteria, the selection criteria based on a coincidence between a data set of expert grades and grades given by said probabilistic neural network during a training process of said probabilistic neural network.

17. The apparatus according to claim 16, wherein the neural network computation platform comprises plurality of probabilistic neural networks, wherein a grade determined by a selected probabilistic neural network from said plurality having a highest value of grading quality according to a selection criteria, the selection criteria based on a coincidence between a data set of expert grades and grades given by said selected probabilistic neural network during a training process of said probabilistic neural network.

* * * * *